United States Patent [19]

Strehlke et al.

[11] 4,113,780

[45] Sep. 12, 1978

[54] EXTRACTIVE DISTILLATION OF ACETONE

[75] Inventors: Günter Strehlke, Rheinkamp-Baeri; Günther Osterburg, Homberg, both of Fed. Rep. of Germany

[73] Assignee: Deutsche Texaco Aktiengesellschaft, Hamburg, Fed. Rep. of Germany

[21] Appl. No.: 547,846

[22] Filed: Feb. 6, 1975

[30] Foreign Application Priority Data

Feb. 7, 1974 [DE] Fed. Rep. of Germany ....... 2405730

[51] Int. Cl.$^2$ ............................................. C07C 45/24
[52] U.S. Cl. .................................. 260/593 P; 203/62
[58] Field of Search ..................................... 260/593 P

[56] References Cited

U.S. PATENT DOCUMENTS

| | | | |
|---|---|---|---|
| 3,031,384 | 4/1962 | Sirois et al. | 260/593 P |
| 3,419,477 | 12/1968 | Mattia | 260/593 P |
| 3,764,627 | 10/1973 | Prinz | 260/593 P |

OTHER PUBLICATIONS

Perry, Chemical Engineers' Handbook, 4th Edn., pp. 13–46 to 13–51.

*Primary Examiner*—James O. Thomas, Jr.
*Assistant Examiner*—James H. Reamer
*Attorney, Agent, or Firm*—Thomas H. Whaley; Carl G. Ries; William E. McNulty

[57] ABSTRACT

Acetone containing less than 0.2 weight percent water is produced in an extractive distillation of acetone containing appreciable quantities of water by utilizing isopropyl alcohol as the extracting agent.

6 Claims, No Drawings

EXTRACTIVE DISTILLATION OF ACETONE

BACKGROUND OF THE INVENTION

The present invention relates to a process for producing practically anhydrous acetone by means of extractive distillation, the acetone being contained in reaction mixtures derived for example, from the synthesis of acetone from isopropyl alcohol and the synthesis of methylisobutyl ketone from acetone. More particularly, this invention relates to a process using isopropyl alcohol as the extracting agent in the purification of acetone by distillation, wherein the isopropyl alcohol is recycled and may be present in the afore-mentioned reaction mixtures.

Numerous proposals have been made to remove water from acetone which may have been prepared by different methods. These proposals usually are related to the particular production process, that is, the raw product mixture which is produced is treated to yield the desired products and these products are further treated for maximum purity. Thus, the preparation of acetone from isopropyl alcohol, ethanol, acetylene, acetaldehyde or acetic acid by dehydrogenation, oxidation, or catalytic hydrogenation in the vapor phase generally yields acetone vapor in admixture with different vapors. German Auslegeschrift No. 1,012,909 proposes a simplified distillation process for removing acetone from the afore-mentioned vapor mixtures and dehydrating it by passing the mixture of hot gases and vapors derived from the acetone synthesis through a column in counter-current flow direction relative to a liquid flowing downward, using the sensible and latent heat of the gases and vapors for concentrating the acetone and removing it from the remaining acetone-containing liquids. The water content of the acetone so obtained ranges from 0.02 to 0.10 weight percent.

German Auslegeschrift No. 1,266,746 proposes to remove acetone from a mixture containing acetone, methyl acetate and methanol by subjecting the mixture to a predistillation to remove higher-boiling components therefrom, taking into consideration that the hydrocarbons which are present interfere with the extractive distillation by means of water; the overhead product obtained from the predistillation is subjected to a liquid-liquid extraction using water, and the layer of lighter hydrocarbons is removed; finally, the aqueous extract is subjected to extractive distillation with water, the bottoms product obtained is subjected to fractional distillation, and acetone, containing 0.43 weight percent water, is obtained as the overhead product.

Other methods for removing water from acetone or for concentrating aqueous acetone fluids have been disclosed in German Auslegeschrift No. 1,793,516 and German Offenlegungschrift No. 2,047,614. The process disclosed in said German Auslegeschrift employs molecular sieves using zeolites, having pore diameters ranging from 4 to 5A, to free the acetone from methanol, water, and other contaminants. In order to reduce formation of by-products when the acetone comes in contact with the zeolite, it is necessary to employ specific contacting times and contacting temperatures. According to the above mentioned German Offenlegungsschrift, the pervaporation technique (evaporation through a membrane) is employed in order to obtain a "pure" acetone containing 0.5 wt.% water.

The object of the present invention is to dehydrate an acetone of the type occurring, for example, in reaction mixtures derived from the catalytic dehydrogenation of isopropyl alcohol and from the methylisobutyl ketone synthesis of acetone including condensation, dehydration, and hydrogenation, to a water content of less than 0.2 weight percent.

Another object of this invention is to remove the water by the use of a reaction component of the reaction mixtures occurring in the conventional acetone production process.

Finally, it is an object of this invention to remove the water from acetone by an economical manner in existing plants taking environmental factors into account.

SUMMARY OF THE INVENTION

After removing volatile by-products in a predistillation, acetone-containing reaction mixtures are processed to produce acetone containing less than 0.2 weight percent water in an extractive distillation process utilizing isopropyl alcohol as the extracting agent. Operating conditions include reflux ratios of 2:1 to 10:1 column top pressure of 0.5 to 2.0 atmospheres absolute and additions to the column of 5 to 15 volume percent of isopropanol (based on the column load).

DESCRIPTION OF THE PREFERRED EMBODIMENTS

The above objects are achieved by a process for the recovery of a practically anhydrous acetone comprising removing the water by distillation wherein the acetone-containing reaction mixtures derived from conventional acetone production processes are freed from volatile byproducts by predistillation, characterized by introducing the bottoms product from the predistillation process into the stripping section of the distillation column and subjecting the water-containing acetone vapors to an extractive distillation by passing isopropyl alcohol to the rectifying section of the column while operating the column at reflux ratios of from 2:1 to 10:1 and column top pressures of from about 0.5 to about 2.0 atmospheres (absolute).

According to a preferred embodiment of the process of our invention, the acetone which is contained in the reaction mixtures resulting from the preparation of acetone from isopropyl alcohol and, optionally, from the preparation of methylisobutyl ketone from acetone, is withdrawn as the overhead product with less than 0.2 weight percent of water subsequent to predistillation and extractive distillation, and the isopropyl alcohol passing into the bottoms product, derived from the extraction distillation is recycled, after having been removed from said bottoms product, to the acetone production process and/or in part to the extraction distillation.

The process of this invention may be used generally in conventional acetone production processes such as the prior art processes mentioned above. The process of this invention is described in greater detail by reference to reaction mixtures such as those occurring, for example, in the synthesis of acetone by catalytic dehydrogenation of isopropyl alcohol as well as the synthesis of methylisobutyl ketone from acetone by condensation, dehydration, and hydrogenation. A restriction of the subject matter of this invention to the combined treatment of these reaction mixtures is not contemplated, the composition of these mixtures, however, allows for the advantage of simultaneous treatment. The products contained in the reaction mixtures include mainly acetone, water, isopropanol, and methylisobutyl ketone (MIBK). The removal of pure acetone and pure MIBK is carried out in a common acetone-MIBK distillation unit where lighter boiling, lower hydrocarbons, acetone, water, isopropyl alcohol, MIBK, and higher ketones are separated in series-connected columns. The acetone column used in the conventional distillation process employed heretofore yielded an acetone product containing water in an amount of about 0.5 weight percent.

Prior to entering the unit, raw MIBK and raw acetone, or raw acetone alone, derived from their respective synthesis processes, are mixed in a charge vessel and the mixture is then freed, in a preliminary column, from volatile by-products including mainly hydrocarbons having up to 6 carbon atoms. The acetone-MIBK mixture which passes from the preliminary column and is introduced into the acetone column may be characterized by the following typical compositions:

|  | Feed No. 1[1] wt. % | Feed No. 2[2] wt. % |
|---|---|---|
| Water | 0.5 | 2.4 |
| Dimethyl ketone | 79.0 | 69.7 |
| Isopropanol | 19.0 | 13.6 |
| MIBK | 1.3 | 13.5 |
| Di-isobutyl ketone | — | 0.3 |
| Methylisobutyl carbinol + Mesityl oxide | 0.2 | 0.5 |

[1]Composition of the raw acetone obtained from the synthesis after prepurification.
[2]Average composition of the combined reaction mixtures obtained from the acetone and MIBK syntheses, after prepurification.

EXAMPLE I

This example demonstrates the limitations of producing low water-content acetone by conventional distillation techniques.

The tests were carried out in a continuously operated bubble-cap tray column, using up to 94 bubble trays for a charge of up to 0.6 liters per hour. The tray efficiency for the type of column used was 70 percent. Tray efficiency depends on the given column design and indicates the percentage of the selectivity of an ideal tray (theoretical separation stage) per column tray. The technical equipment was designed for tests using from 0.5 to 2.0 atm. abs. based on the column top pressure. Under all test conditions, it was possible to draw samples from the various column sections, so that concentration profiles along the column could be obtained. The bottoms product was withdrawn continuously.

The withdrawal of overhead product and the reflux ratio were controlled by a vibrating funnel. The feed was preheated to column temperature and introduced into the column. The water content in the acetone was determined in accordance with the OH valence vibration at 1.89μ. As compared to the conventional method of Karl Fischer (DIN 51 777 or ASTM D-1364), the foregoing method provided greater accuracy, the sample volume was smaller, and less time was required.

Eight tests were performed without extractive distillation to investigate the influence of the following parameters on the water content of the overhead product:
1. pressure: 1.3; 1.0; 0.7 atm. abs.
2. reflux ratio: 4:1, 3:1, 10:1
3. length of column: 54; 69; 94 trays
4. temperature profile along the column Feed No. 1 was used in Tests No. 1 and 4; feed No. 2 was used in the remaining six tests. The feed rate in each test was maintained to provide a column load of 2 liters/hr. (Column load is defined as the amount of liquid material passing through the upper portion of the column per unit time, i.e. the quantity of vapor leaving the top of the column. Column load ist equal to the sum of the overhead product and the reflux returned to the column).

The eight tests, including test conditions and results, are summarized in Table I.

TABLE I

| PARAMETER | COMPARATIVE TESTS TEST NO. | | | | | | | |
|---|---|---|---|---|---|---|---|---|
| | 1 | 2 | 3 | 4 | 5 | 6 | 7 | 8 |
| Column top pressure, atm. abs. | 0.7 | 0.7 | 1.0 | 1.3 | 1.0 | 1.0 | 1.0 | 1.0 |
| Reflux Ratio | 3:1 | 4:1 | 4:1 | 4:1 | 4:1 | 4:1 | 4:1 | 10:1 |
| Length of column (actual trays) | 69 | 69 | 69 | 69 | 54 | 94 | 54 | 69 |
| Temperature at 12th tray, °C | 53 | 53 | 65 | 73 | 62 | 64 | 74 | 64 |
| Water content in overhead product, wt. % | 0.12 | 0.08 | 0.25 | 0.43 | 0.31 | 0.19 | 0.45 | 0.08 |

The results show that by merely adding to the length of the column at a distillation pressure of 1.3 atm. abs., it is not possible to achieve the desired goal. The maximum removal of water from acetone by distillation can be effected either by distillation at reduced pressure, a pressure reduction to 0.7 atm. abs., resulting in a decrease in the production capacity of the column by one half as compared to an operation at 1.3 atm. abs., or by increasing the recycle ratio from 4:1 to at least 10:1, also resulting in a decrease in the production capacity. Apart from that, acetone distillation conducted under reduced pressure involves a low dew point and hence a serious environmental hazard.

Surprisingly, it has been found that the aforementioned problems may be resolved by conducting the recovery of a low water pure acetone (water content less than 0.2 weight percent) using isopropyl alcohol (water content of 0.1 weight percent maximum) as the agent in an extractive distillation and introducing said agent at a randomly selected point into the rectifying portion of the acetone column. In continuous distillation processes that portion of the column situated between the charge material inlet and the top of the column is designated as the rectifying section and that portion between the charge inlet and the bottom of the column is designated as the stripping section. By adjusting the temperature of the isopropyl alcohol to the temperature of the charge tray (boiling temperature of the acetone) uncontrolled recycling in the column is prevented. The downward flowing isopropyl alcohol extracts the major portion of the water contained in the upward flowing acetonewater vapor mixture depending on the amount of isopropyl alcohol and the extraction section of the column. The extracted water together with the isopropyl alcohol, passes into the bottom section of the column. The small amounts of the isopropyl alcohol passing into the upward flowing vapor are separated from the acetone in the remaining upper portion of the column. The isopropyl alcohol present in the bottoms product of the acetone column, after having separated, is recycled in part to the acetone synthesis, and a partial stream is passed to the rectifying section of the column for use in another extraction distillation operation. The amount of isopropyl alcohol required is relatively low and in the afore-mentioned tests amounted to from 5 to 15 volume percent, preferably about 10 volume percent, based on the load of the column.

EXAMPLE II

A series of three tests demonstrating the process of this invention were conducted in the equipment used in Example I, modified where necessary to permit the introduction of an extracting agent into the rectifying section. In addition, the number of trays in the column used in this series of tests was 69, 94 or 110. In each of the tests, the minimum water content of the overhead product was evaluated without extractive distillation and then extractive distillation, using isopropanol alcohol, was conducted to evaluate the effect on the water content of the acetone product. In test No. 9 and 10, feed No. 2 was the charge stock while in test No. 11, the acetone feed to the column was feed No. 1. In all runs the feed rate was adjusted to maintain the column load at 2 liters/hour. The isopropyl alcohol used as the extracting agent in tests No. 9 and 10 had a water content of 0.1 weight percent while that used in test No. 11 had a water content of 0.01 weight percent (100 ppm). In test No. 10 the effect of increasing the amount of extracting agent and extraction trays was investigated. The extraction section (the extraction trays) is that portion of the column in the rectifying section between the acetone feed inlet and the isopropyl alcohol addition inlet. The isopropyl alcohol recovered from the bottoms of the column was recycled subsequent to dehydration to reduce the amount of fresh extracting agent required.

The results of these extraction distillation tests are shown in Table II.

TABLE II

Extractive Distillation of Acetone by means of Isopropyl Alcohol

|  | Test No. 9 | Test No. 10 | Test No. 11 |
|---|---|---|---|
| Number of trays | 69 | 94 | 110 |
| Column top pressure, atm. abs. | 1.3 | 1.3 | 1.0 |
| Stripping trays | 12 | 12 | 12 |
| Rectifying trays | 57 | 82 | 98 |
| Reflux Ratio | 4:1 | 4:1 | 4:1 |
| Water Content, wt. %[1] | 0.5 | 0.42 | 0.3 |

|  |  | A | B | C |  |
|---|---|---|---|---|---|
| Vol. % Isopropyl alcohol relative to column load | 10 | 10 | 5 | 5 | 10 |
| Extraction trays | 30 | 42 | 42 | 52 | 58 |
| Water Content, wt. %[2] | 0.12 | 0.08 | 0.16 | 0.12 | 0.01 |

[1] Water content of acetone product without extractive distillation.
[2] Water content of acetone product after extractive distillation according to invention.

These results show the following advantages of the procedure according to this invention: There is no substantial reduction in the production capacity since the column may be operated at a reasonable recycle ratio (4 : 1) and a reasonable pressure (1.3 atm. abs.). The extraction effect may be influenced by varying the number of extraction trays or the amount of isopropyl alcohol employed for the extraction. Further, reducing the water content of the isopropyl alcohol results in a reduction in the water content of the acetone product.

The process of this invention may be used in all acetone distillation processes where low content acetone is to be obtained from a water-containing acetone feed mixture. In one such process the raw acetone feed, containing both water and isopropyl alcohol, is obtained in the synthesis of acetone by the dehydrogenation of isopropyl alcohol.

We claim:

1. A process for the production of low water content acetone from a feed comprising acetone and water, said feed having been distilled, if necessary, to remove $C_6$ and lighter volatile material therefrom, which comprises
    (a) introducing the feed into the top of the stripping section of a distillation column comprising a rectifying section and a stripping section under distillation conditions comprising a reflux ratio of 2:1 to 10:1 and a column top pressure of 0.5 to 2.0 atmospheres absolute,
    (b) introducing isopropyl alcohol, having a water content of 0.1 weight percent maximum, into the rectifying section intermediate the feed inlet and the column top whereby the water-containing acetone is subjected to extractive distillation by said isopropyl alcohol, said isopropyl alcohol addition being 5 to 15 volume percent of the column load,
    (c) recovering from the overhead from said column as the product therefrom acetone having a maximum water content of less than 0.2 weight percent, and
    (d) recovering from the bottoms from said column a product comprising isopropyl alcohol and water.

2. A process according to claim 1 wherein the isopropyl alcohol of step (b) comprises the isopropyl alcohol recovered in step (d).

3. A process according to claim 1 wherein the isopropyl alcohol of step (b) comprises 0.1 weight percent water.

4. A process according to claim 1 wherein the isopropyl alcohol of step (b) comprises about 0.01 weight percent water and the acetone of step (c) comprises about 0.01 weight percent water.

5. A process according to claim 1 wherein the reflux ratio is about 4:1, the column top pressure is about 1.3 and the isopropyl alcohol of step (b) is about 10 volume percent of column load.

6. A process according to claim 1 wherein the feed is selected from the group consisting of acetone-containing reaction mixtures from acetone synthesis by dehydrogenation of isopropyl alcohol and acetone-containing reaction mixtures from methylisobutyl ketone synthesis from acetone by condensation, dehydration and hydrogenation.

* * * * *